United States Patent [19]

Yoshimoto et al.

[11] Patent Number: 4,474,945

[45] Date of Patent: Oct. 2, 1984

[54] ANTHRACYCLINE ANTIBIOTICS

[75] Inventors: Akihiro Yoshimoto, Fujisawa; Hiroyasu Tobe, Tokyo; Tomoyuki Ishikura, Chigasaki; Hamao Umezawa; Tomio Takeuchi, both of Tokyo, all of Japan

[73] Assignee: Sanraku-Ocean Co., Ltd., Tokyo, Japan

[21] Appl. No.: 405,917

[22] Filed: Aug. 6, 1982

[30] Foreign Application Priority Data

Aug. 11, 1981 [JP] Japan .................................. 56-125826
Jun. 21, 1982 [JP] Japan .................................. 57-107256

[51] Int. Cl.$^3$ ...................... C07H 17/08; C12P 19/62; C12N 1/00
[52] U.S. Cl. ..................................... 536/6.4; 424/180; 424/181; 435/78; 435/172.3

[58] Field of Search ......................................... 536/6.4

[56] References Cited

U.S. PATENT DOCUMENTS

| | | | |
|---|---|---|---|
| 4,309,503 | 1/1982 | Cassinelli et al. | 536/6.4 |
| 4,329,339 | 5/1982 | Fujiwara et al. | 536/6.4 |
| 4,355,026 | 10/1982 | Umezawa et al. | 536/6.4 |
| 4,373,094 | 2/1983 | Oki et al. | 536/6.4 |
| 4,386,198 | 5/1983 | Oki et al. | 536/6.4 |

Primary Examiner—Johnnie R. Brown
Attorney, Agent, or Firm—James J. Ralabate

[57] ABSTRACT

New anthracycline compounds, 2-hydroxyaclacinomycin B having potent antitumor activity and lower toxicity, and a process for producing 2-hydroxyaclacinomycins A, B, and N by fermentation.

1 Claim, No Drawings

ANTHRACYCLINE ANTIBIOTICS

BACKGROUND OF THE INVENTION (1) Field of the Invention

The present invention relates to a novel anthracycline glycoside and a process for the production of the related compounds.

More particularly, the present invention relates to a novel anthracycline glycoside, 2-hydroxyaclacinomycin B of the general formula

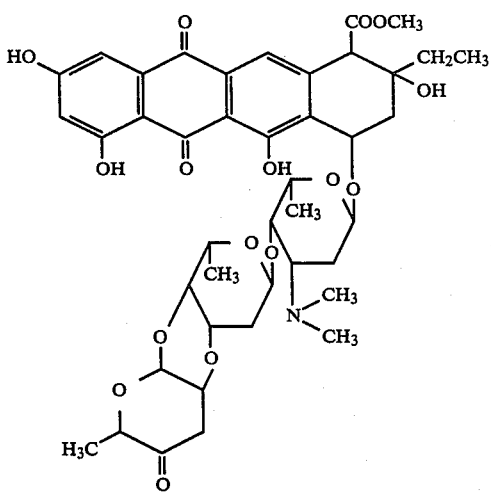

and to a process for the production of 2-hydroxyaclacinomycins A, B, and N by fermentation.

(2) Description of the Prior Art

A number of anthracycline glycosides have been found in the culture medium of Streptomyces, and are described in prior literatures. Among them, daunomycin and adriamycin have already been clinically applied for human cancers.

Rhodomycinones, iso-rhodomycinones and rhodomycin-related antibiotics are described in Chem. Ber. 88, 1792–1818 (1955); Chem. Ber. 101, 1341–1348 (1968); J. Med. Chem., 20, 957–960 (1977); Pharmazie 27, 782–789 (1972); Zeit. Allg. Mikrobiol., 14, 551–558 (1974); Tetrahed. Lett. No. 38, 3699–3702 (1973); Folia Microbiol., 24, 293–295 (1979); and J. Antibiotics, 32, 420–424 (1979).

Aclacinomycin A is disclosed in U.S. Pat. No. 3,988,315 and by Oki et al. in J. Antibiotics 28, 830 (1975) and 32, 791–812 (1979).

Cinerubins A and B are disclosed in U.K. Pat. No. 846,130, U.S. Pat. No. 3,864,480, Keller-Schierlein et al., "Antimicrobial Agents and Chemotherapy", page 68 (1970), Chemical Abstracts 54, 1466i (1960) and J. Antibiotics 28, 830 (1975).

2-Hydroxyaclacinomycin A is disclosed in European Patent Application Publication No. 30255.

Further illustrative and summary disclosures of anthracycline antibiotics can be located in Index of Antibiotics from Actinomycetes, Hamao Umezawa, Editor-in-Chief, University Park Press, State college, Pennsylvania, U.S.A. (1967) as follows:

| Antibiotics | Page numbers |
| --- | --- |
| Aclacinomycins A and B | 101–102 |
| Adriamycin | 122 |

-continued

| Antibiotics | Page numbers |
| --- | --- |
| Carminomycin I | 225 |
| Galirubins A - D | 405–408 |
| Rhodomycins X - Y | 879–880 |
| β-Rhodomycins | 881–885 |
| γ-Rhodomycins | 886–892 |
| Steffimycin | 945 |

The textbooks, Antibiotics, Volume 1, Mechanisms of Action, edited by David Gottlieb and Paul D. Shaw, Springer-Verlag New York, Inc., N.Y. (1967) at pages 190–210 contains a review by A. DiMarco entitled "Daunomycin and Related Antibiotics".

Information Bulletin, No. 10, International Center of Information of Antibiotics, in collaboration with WHO, December, 1972, Belgium, reviews anthracyclines and their derivatives.

SUMMARY OF THE INVENTION

The novel anthracycline glycoside according to the present invention includes 2-hydroxyaclacinomycin B and the non-toxic acid addition salt thereof.

Other embodiments of the present invention provide a new producing 2-hydroxyaclacinomycins A, B, and N by cultivating a microorganism of Streptomyces capable of producing the anthracycline compounds is cultivated in a nutrient medium whereby the compounds are recovered from the broth.

Still other embodiments of the present invention provide a recombinant capable of producing 2-hydroxyaclacinomycins A, B, and N which is fostered by protoplast-fusing a mutant of Streptomyces galiaeus MA 144-$M_1$ capable of accumulating 2-hydroxyaklavinone with a mutant of Streptomyces galilaeus MA 144-$M_1$ capable of converting 2-hydroxyaklavinone to 2-hydroxyaclacinomycin A in spite of no ability to produce anthracyclinone.

DETAILED DESCRIPTION OF THE INVENTION

This invention relates to 2-hydroxyaclacinomycin B, a new antitumor anthracycline antibiotic and a method for preparation of 2-hydroxyaclacinomycins A, B, and N.

Aclacinomycin A produced by Streptomyces galilaeus MA 144-$M_1$ (ATCC 31133) is an antitumor antibiotic which is useful in the therapy of leukemia and solid tumors (cf. U.S. Pat. No. 3,988,315). In addition, the present inventors have filed a patent application for 2-hydroxyaclacinomycin A, an analog of aclacinomycin A, presented by the formula

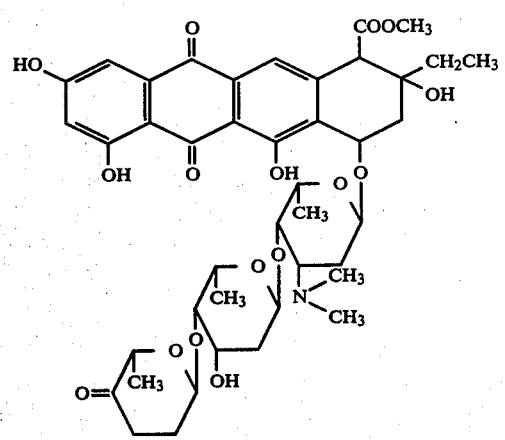

(cf. European Publication No. 30255), as it has a stronger antitumor activity, but is less cardio-toxic, than aclacinomycin A.

In the latter patent specification, 2-hydroxyaclacinomycin A is produced by a two-step process in which 2-hydroxyaklavinone presented by the formula

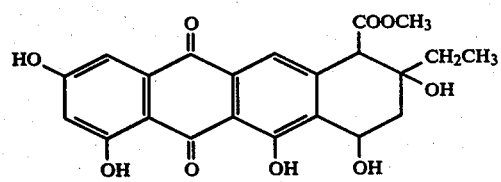

is obtained by fermentation of a mutant of *Streptomyces galilaeus* MA 144-M$_1$ and 2-hydroxyaklavinone is then converted to 2-hydroxyaclacinomycin A by an antibiotic-non-producing mutant of *Streptomyces galilaeus* MA 144-M$_1$ capable of glycosidating the anthracyclinone.

In order to improve the above-described two-step fermentation method for preparation of 2-hydroxyaclacinomycin A, the inventors have searched for a microorganism capable of producing the antibiotic by direct fermentation. As a result, they have succeeded in obtaining a recombinant capable of producing directly 2-hydroxyaclacinomycin A by protoplast-fusing the 2-hydroxyaklavinone-producing mutant with the antibiotic-non-producing, anthracyclinone-glycosidating mutant.

In addition to 2-hydroxyaclacinomycin A, the present inventors have found that the recombinant can produce 2-hydroxyaclacinomycin N, a reduction product of 2-hydroxyaclacinomycin A, presented by the formula (cf. European Publication No. 45474)

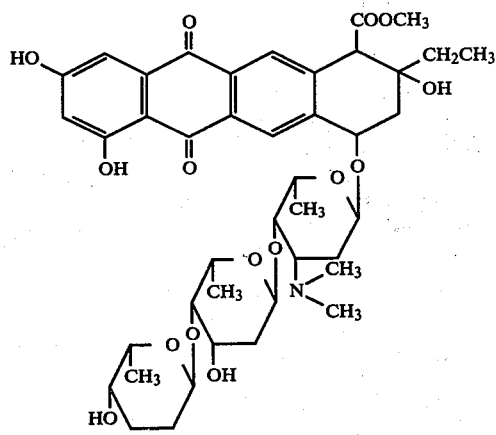

and a hitherto-undescribed anthracycline compound designated 2-hydroxyaclacinomycin B presented by the formula

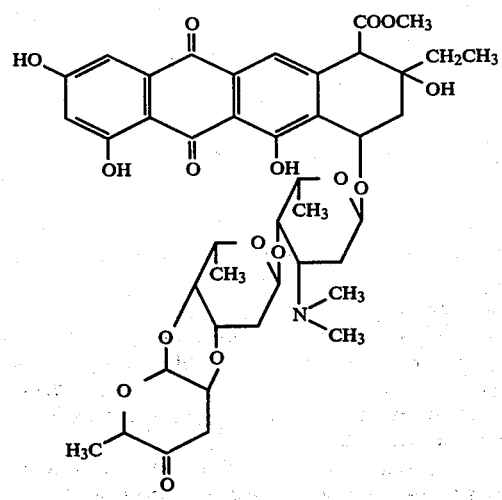

The last anthracycline antibiotic is also proved to have a marked antitumor activity.

2-Hydroxyaclacinomycins A, B, and N provided by this invention can be favorably used as an anticancer agent because of its patent antitumor activity against murine leukemia L1210 and various experimental tumors with low toxicity, as detailed later.

According to this invention, 2-hydroxyaclacinomycins A, B, and N can be produced by any microorganism of various genera, as far as it has an ability to produce the anthracycline compounds by direct fermentation. In general, Streptomyces species are favorable. More particularly, a recombinant of *Streptomyces galilaeus* such as *Streptomyces galilaeus* A-862 which is obtained by the protoplast fusion technique is advantageously employed in this invention.

The protoplast fusion technique has widely been used for preparation of recombinants of various microorganisms including streptomycetes. However this is the first report to describe the recombination of *Streptomyces galilaeus*. More particularly, there is no paper in the literature in which the protoplast fusion technique is applied to fosterage of a recombinant that differs from the parent strains in productivity of antibiotic, without damaging the useful characteristics of the individual parent strains.

Examples of the parent mutants for fostering a recombinant capable of producing 2-hydroxyaclacinomycins A, B, and N by protoplast fusion are a 2-hydroxyaklavinone-accumulating mutant of *Streptomyces galilaeus* MA 144-$M_1$ such as *Streptomyces galilaeus* 10U-2936 (this mutant was isolated by the same method as described for *Streptomyces galilaeus* ANR 58 (FERM P-5081) in Japan Kokai No. 56-49341/1981) and an antibiotic-non-producing, anthracyclinone-glycosidating mutant of *Streptomyces galilaeus* MA 144-$M_1$ such as *Streptomyces galilaeus* 11U-111 (this mutant was isolated by the same method as described for *Streptomyces galilaeus* KE-303 (FERM P-4808) in Japan Kokai No. 56-15299/1981).

In this invention auxotrophic mutants are favorably employed for easy separation of recombinants. Namely it is easy and efficient to select recombinants as heterotrophs on a minimal medium.

In practice, heterotrophic recombinants are then checked for the production of 2-hydroxyaclacinomycins A, B, and N.

In the following, a method for fosterage and isolation of a recombinant capable of producing 2-hydroxyaclacinomycins A, B, and N is explained in detail.

The following two auxotrophic mutants were derived from *Streptomyces galilaeus* MA 144-$M_1$ by mutation for subsequent recombination experiments using the protoplast fusion technique:

Strain 10U-2936: $ACM^-$, $AKN^-$, $2HO\text{-}AKN^+$, $Glyc^-$, $ade^-$

Strain 11U-111: $ACM^-$, $AKN^-$, $2HO\text{-}AKN^-$, $Glyc^+$, $ura^-$

Below-listed are the meanings of the abbreviated genetic markers adopted in the present invention.

$ACM^-$: no production of aclacinomycin
$AKN^-$: no production of aklavinone
$2HO\text{-}AKN^+$: production of 2-hydroxyaklavinone
$2HO\text{-}AKN^-$: no production of 2-hydroxyaklavinone
$Glyc^+$: ability to convert exogenously-added aklavinone or 2-hydroxyaklavinone to aclacinomycin or 2-hydroxyaclacinomycin, respectively, by endogenous glycosidation
$Glyc^-$: no ability to convert exogenously-added aklavinone or 2-hydroxyaklavinone to aclacinomycin or 2-hydroxyaclacinomycin, respectively, by endogenous glycosidation
$ade^-$: requirement of adenine for growth
$ura^-$: requirement of uracil for growth One loopful of mature spores were collected from each culture of the two mutants on YS agar medium; inoculated into a test tube containing sterile YS broth (0.3% yeast extract, 1.0% soluble starch; pH 7.2; 4 ml/tube) and incubated overnight at 28° C. Three-tenths milliliter of the culture was transferred into a 250 ml Erlenmeyer flask containing 30 ml of MSG medium (Okanishi et al.; J. Gen. Microbiol. 80: 389, 1974) and shake-cultured at 28° C. for 20 hours on a rotary shaker (220 rpm). Twenty milliliters of the culture was centrifuged to give mycelia which were then washed with 10 ml of P medium (cf. J. Gen. Microbiol. 80: 389, 1974). The washed mycelia were suspended in 20 ml of P medium containing 1 mg/ml of lysozyme (Sigma Chemical Co.) and allowed to stand at 28° C. for one hour. After passing through a glass tube (15×200 ml) packed with sterile defatted cotton, the filtrate was centrifuged at a low temperature (1000×g, 10 minutes) to give protoplasts. The protoplasts were taken in 1.5 ml of P medium and diluted with P medium until the optical density of the suspension reached 1.0 at 600 nm. The protoplast densities of strain 10U-2936 and strain 11U-111 were found to be $4.4 \times 10^6$ colony-forming units/ml and $1.1 \times 10^6$ CFU/ml respectively. They were mixed at a ratio of 10:1 for protoplast fusion.

Two-tenths milliliter of the protoplast mixture was added to 1.8 ml of P medium containing 40% polyethylene glycol (abbreviated to PEG hereafter) 4000; gently mixed and allowed to stand at 28° C. for 5 minutes. After appropriate dilution in P medium, the protoplast suspension was plated both on a minimal medium and on a complete medium containing 100 μg/ml each of adenine and uracil, and incubated at 28° C. for 10 days.

| Minimal medium | |
|---|---|
| Sucrose | 110 g |
| Polyethylene glycol 1000 | 50 g |
| $K_2SO_4$ | 0.25 g |
| Trace elements solution* | 2 ml |
| $KH_2PO_4$** | 0.05 g |
| $MgCl_2.6H_2O$ | 4.06 g |
| $CaCl_2.2H_2O$** | 2.95 g |
| Glucose | 10 g |
| L-Asparagine | 3 g |
| 0.1 M TES, pH 7.4** | 100 ml |
| Agar | 22 g |
| To make a total of 1 liter with distilled water | |

*$ZnCl_2.4H_2O$ 40 mg; $FeCl_2.6H_2O$ 200 mg; $CuCl_2.2H_2O$ 10 mg; $MnCl_2.4H_2O$ 10 mg; $Na_2B_4O_7.10H_2O$ 10 mg; $(NH_4)_6(Mo_7O_{24}).4H_2O$ 10 mg; dissolved in 1 liter of distilled water
**Sterilized separately About 500 colonies on the minimal medium were transferred onto minimal agar slants having the following composition. After incubation at 28° C. for 5 days, each culture was again transferred onto a minimal agar slant.

| Minimal agar slant | |
|---|---|
| Glucose | 10 g |
| L-Asparagine | 3 g |
| $KNO_3$ | 1 g |
| $K_2HPO_4$ | 0.5 g |
| $MgSO_4.7H_2O$ | 0.5 g |
| $CaCl_2.2H_2O$ | 0.5 g |
| 0.1 M Tris-HCl, pH 7.2 | 100 ml |
| Agar | 15 g |
| To make a total of 1 liter with distilled water | |

One loopful of the culture was inoculated into a test tube containing YS broth (described hereinbefore) and shake-cultured overnight at 28° C. The whole culture was inoculated into a 250 ml Erlenmeyer flask containing 30 ml of fermentation medium having the following composition and allowed to grow for 2 days on the rotary shaker (described hereinbefore).

| Fermentation medium | |
|---|---|
| Soluble starch | 1.5% |
| Glucose | 1.0% |
| Soybean meal | 3.0% |
| Yeast extract | 0.2% |
| $K_2HPO_4$ | 0.1% |
| $MgSO_4.7H_2O$ | 0.1% |
| NaCl | 0.3% |
| Minerals solution* | 0.125% |

-continued

| Fermentation medium | |
| --- | --- |
| Tap water | pH 7.4 |

*CuSO$_4$.5H$_2$O 2.8 g; FeSO$_4$.7H$_2$O 0.4 g; MnCl$_2$.4H$_2$O 3.2 g; ZnSO$_4$.7H$_2$O 0.8 g; dissolved in 500 ml of distilled water For product analysis, 5 ml of the broth was sampled and mixed with 5 ml of a 3:2 mixture of chloroform and methanol on a magnetic mixer. After centrifugation, the chloroform layer was recovered and concentrated to dryness. The residue was dissolved in a small volume of chloroform and spotted 1.5 cm from the bottom on a pre-coated silica gel thin layer chromatographic plate (E. Merck, Darmstadt). The plate was developed in a solvent system of chloroform/methanol/conc. ammonia (150/11/0.3). The production of 2-hydroxyaclacinomycins was judged by comparison with the authentic samples of 2-hydroxyaclacinomycin A and 2-hydroxyaklavinone simultaneously developed on the same plate. Among 500 isolates, 420 were antibiotic-non-producers and 40 were 2-hydroxyaklavinone producers, while 30 recombinants produced 2-hydroxyaclacinomycins.

Among the 2-hydroxyaclacinomycin producers, *Streptomyces galilaeus* A-862 was found to be the most suitable for production of the anthracycline antibiotics of the present invention. This recombinant has been deposited at the Fermentation Research Institute, Agency of Industrial Science and Technology, Japan, with an access number of FERM MP-45 according to the Budapest Treaty on the International Recognition of the Deposit of Microorganisms for the Purposes of Patent Procedure.

The microbiological characteristic of this recombinant are largely the same as those of the parent strain, *Streptomyces galilaeus* MA 144-M$_1$ (cf. Japan Kokai No. 51-34915/1976).

The microbiological properties of strain A-862 are described as follows:

(1) Morphology

Straight, hooked or helical aerial mycelia stretch from well-branched substrate mycelia. Especially on starch-inorganic salts agar, abundant hooked or helical aerial mycelia are observed. No whirl forms.

Mature spore chain consists of more than 10 spores. Spore is 0.4–0.8×0.8–1.6μ in size and has a smooth surface. No aerial mycelium grows on most media except yeast extract-malt extract agar and starch-inorganic salts agar where poor aerial mycelia form without sporulation.

(2) Cultural properties on various media

The color designations in parenthesis are in accordance with the definitions of the Color Harmony Manual (Container Corporation of America) and subsidiarily refer to the Color Standards of Japan Color Institute.

(1) Sucrose-nitrate agar (incubated at 27° C.)
Vegetative growth: colorless or pal yellow (2db)
Aerial mycelium: none
Soluble pigment: none (2) Glucose-asparagine agar (incubated at 27° C.)
Vegetative growth: light orange yellow (3ea) to light brown (4ie)
Aerial mycelium: scanty
Soluble pigment: slight in yellowish brown (3) Glycerin-asparagine agar (ISP-5 medium; incubated at 27° C.)
Vegetative growth: pale yellow (2db) to yellowish brown
Aerial mycelium: very scanty
Soluble pigment: none (4) Starch-inorganic salts agar (ISP-4 medium; incubated at 27° C.)
Vegetative growth: pale yellow (2db) to yellowish brown
Aerial mycelium: light gray (d)
Soluble pigment: none (5) Tyrosine agar (ISP-7) medium; incubated at 27° C.)
Vegetative growth: light olive (2ge) to grayish brown (4ig)
Aerial mycelium: none
Soluble pigment: brown (6) Nutrient agar (incubated at 27° C.)
Vegetative growth: yellowish brown
Aerial mycelium: yellowish gray (2dc) to light gray (d)
Soluble pigment: slight in brown (7) Yeast extract-malt extract agar (ISP-2 medium; incubated at 27° C.)
Vegetative growth: light orange yellow (3ea) to light brown (4ie)
Aerial mycelium: yellowish gray (2dc)
Soluble pigment: red (8) Oatmeal agar (ISP-3 medium; incubated at 27° C.)
Vegetative growth: yellowish brown to grayish yellow (3ec)
Aerial mycelium: almost none
Soluble pigment: slight in brown (3) Physiological properties This recombinant can not be differentiated from the parent strains in physiological properties such as gelatin digestion, melanoid formation, starch hydrolysis, peptonization of skim milk, utilization pattern of carbon sources, etc. The physiological properties of strain A-862 are summarized as follows:

(1) Growth temperature

When examined at temperatures of 20° C., 24° C., 27° C., 30° C., 37° C. and 50° C. on maltose-yeast extract agar (maltose 1.0%, yeast extract (Oriental Yeast Co.) 0.4%, agar 2.0%; pH 6.0), this recombinant can grow at the tested temperatures except 50° C., the optimum temperature being in the range of 27° C.–37° C.

(2) Liquefaction of gelatin (glucose-peptone gelatin; incubated at 20° C.)
Positive.

(3) Hydrolysis of starch (starch-inorganic salts agar; incubated at 27° C.)
Positive.

(4) Coagulation and/or peptonization of skim milk (incubated at 27° C.)
Peptonization without coagulation.

(5) Formation of melanoid pigment (tryptone-yeast extract broth (ISP-1 medium); peptone-yeast extract-iron agar (ISP-6 medium); tyrosine agar (ISP-7 medium); all incubated at 27° C.)
Melanoid pigment formed in all the tested media.

(6) Utilization of carbon sources (Pridham-Gottlieb medium (ISP-9 medium); incubated at 27° C.)
Positive: L-arabinose, D-xylose, glucose, D-fructose, sucrose, inositol, L-rhamnose, raffinose
Negative: D-mannitol For production of 2-hydroxyaclacinomycin B according to this invention, a 2-hydroxyaclacinomycin-producing strain is cultivated by a commonly used method in a medium containing various assimilable nutrient sources. Favorably employed are carbon sources such as glucose, glycerol, sucrose, starch, maltose and fats and oils; organic nitrogen sources such as soybean meal, meat extract, yeast extract, peptone, corn steep liquor and cotton seed meal; and inorganic nitrogen sources such as ammonium sulfate, ammonium chloride, ammonium nitrate and ammonium phosphate. If necessary, inorganic salts such as sodium chloride, potassium chloride, phosphates and heavy metal salts; vitamins; anti-foamers such as Silicone KM 75 (Shinetsu Chemical Co.) and the like may be supplemented.

Fermentation conditions such as temperature, pH, forced aeration and agitation, and fermentation period are selected for the particular strain so suitably that maximum amounts of 2-hydroxyaclacinomycins are accumulated in broth. In practice it is advantageous to ferment at a temperature of 20°–40° C., preferably 28° C., for a period of 1–5 days, preferably 3 days, at a pH of 5–9, preferably 7.4.

For isolation of 2-hydroxyaclacinomycins A, B, and N from fermentation broths, it is common to employ traditional means and methods known in the production of anthracycline antibiotics. For example, the fermentation broth is first separated into the mycelia and the filtrate by centrifugation, or by mixing with a filter aid such as kieselguhr followed by filtration. The myeclia are subjected to extraction with water-miscible solvent such as acetone, methanol, ethanol and butanol, while the filtrate is extracted with organic solvents such as chloroform and ethyl acetate. It is also possible to recover the antibiotics directly from the fermentation broth by a suitable selection of extraction solvents, without preliminary separation of the mycelia from the filtrate.

The organic extracts containing 2-hydroxyaclacinomycins A, B, and N are concentrated to dryness under reduced pressure. For isolation of the individual anthracycline antibiotics, it is advantageous to use singly or in combination various isolation and purification methods such as column chromatography using adsorbents such as silica gel, activated carbon and alumina gel, weakly acidic or basic ion exchange resins and gel-filtration materials such as Sephadex LH-20 (Pharmacia Fine Chemicals AB); preparative silica gel thin layer chromatography; liquid-liquid chromatography; and counter-current distribution.

2-Hydroxyaclacinomycins A, B, and N according to this invention may be in the salt form with inorganic or organic acids. Namely, the free bases of 2-hydroxyaclacinomycins A, B, and N can be converted to their acid addition salts by known methods per se. For example, hydrochloric acid, sulfuric acid, phosphoric acid, hydrobromic acid, nitric acid, acetic acid, propionic acid, maleic acid, citric acid, succinic acid, tartaric acid, fumaric acid, glutamic acid, pantothenic acid, laurylsulfonic acid, benzenesulfonic acid and naphtalenesulfonic acid are favorably used for preparation of the acid addition salts of the anthracycline antibiotics. In practice, the free bases of 2-hydroxyaclacinomycins A, B, and N are treated with the acids in a suitable solvent and their acid addition salts are recovered by freeze-dried or by forced precipitation with a solvent in which the acid addition salts are hardly soluble.

2-Hydroxyaclacinomycins A, B, and N of the present invention markedly inhibit the growth and the nucleic acid synthesis of mouse leukemia cells L1210. For determination of the 50% growth inhibition concentration ($IC_{50}$), $5 \times 10^4$ L1210 cells/ml (final concentration) were inoculated into RPMI 1640 medium (Rosewell Park Memorial Institutes 1640 medium) containing 20% calf serum. The anthracycline compounds of the present invention were added to give a final concentrations from 0.01 μg/ml to 0.25 μg/ml, while the control contained no drug. After incubation at 37° C. in a carbon dioxide incubator, the cell counts of the test and control cultures were measured for calculation of the $IC_{50}$ concentration of antibiotic.

When the effect on nucleic acid synthesis was examined, $5 \times 10^5$ L1210 cells/ml (final concentration) were precultivated at 37° C. for 1–2 hours in a carbon dioxide incubator in RPMI 1640 medium supplemented with 10% calf serum. Fifteen minutes after the anthracycline compounds of the present invention were added at varied concentrations, 0.05 μCi/ml (final concentration) of $^{14}$C-uridine or $^{14}$C-thymidine was added and cultivated at 37° C. for a further 60 minutes. The incorporation of the radioactive base was stopped by addition of 10% trichloroacetic acid. The acid-insoluble matters were recovered; washed three times with 10–5% trichloroacetic acid; and dissolved in formic acid. The radioactivities in the acid-insoluble fractions of the test and control cultures were measured for calculation of the 50% inhibition concentration of antibiotic for nucleic acid synthesis.

The therapeutic effect of 2-hydroxyaclacinomycin B was studied on $CDF_1$ mice bearing L1210 leukemia. From 24 hours after $1 \times 10^5$ L1210 cells/animal were intraperitoneally transplanted to $CDF_1$ mice, 2-hydroxyaclacinomycin B was intraperitoneally given everyday for 10 days. The prolongation of the survival time was calculated relative to the control animals receiving physiological saline as 100. Table 1 compares the in vitro and in vivo activities and toxicities of 2-hydroxyaclacinomycins A, B, and N and aclacinomycin A.

TABLE 1

|  | 2-Hydroxy-aclacino-mycin A | 2-Hydroxy-aclacino-mycin B | 2-Hydroxy-aclacino-mycin N | Aclacino-mycin A |
|---|---|---|---|---|
| 1. Antitumor activity against L1210-bearing mice (dose in mg/kg) | Survival prolongation rate (T/C %) | | | |
| 12 | 120 | 113 | 108 | — |
| 10 | 158 | 139 | 144 | Toxic |
| 7.5 | 220 | 226 | 219 | 123 |
| 5 | 218 | 200 | 202 | 196 |
| 2.5 | 176 | 153 | 148 | 186 |
| 1.25 | 148 | 131 | 128 | 125 |
| 0.63 | 124 | 110 | 109 | 107 |
| 2. In vitro activity against cultured L1210 cells | 50% Inhibition concentration ($IC_{50}$ in μg/ml) | | | |
| Growth inhibition | 0.04 | 0.03 | 0.04 | 0.01 |
| DNA synthesis inhibition | 0.85 | 1.0 | 1.18 | 0.30 |
| RNA synthesis inhibition | 0.14 | 0.22 | 0.18 | 0.04 |
| 3. Toxicity (acute) Mice, i.p. | 50.0 | 50.0 | 45.7 | 22.6 |

The results in Table 1 indicate that 2-hydroxyaclacinomycins A, B, and N are promising antitumor agents, because (1) they kill mouse leukemia cells L1210 at a low concentration and show an excellent survival prolongation effect on mice transplanted with leukemia cells;

(2) they are far less toxic than known anthracycline compounds such as adriamycin and daunomycin; and less toxic than aclacinomycin A which is the least toxic and cardio-toxic among the hitherto-developed anthracycline antibiotics;

(3) their antitumor activity is similar to or better than that of aclacinomycin A; and (4) their dose range for antitumor activity is about 2-fold wider than that of aclacinomycin A.

In general, the primary target of action of anthracycline antiobiotics is nucleic acid synthesis. As 2-hydroxyaclacinomycins A, B, and N of the present invention inhibit RNA synthesis more specifically than DNA synthesis, their mechanism of action resembles that of aclacinomycin and rhodomycin analogs.

The present invention will be explained in detail by the following examples.

EXAMPLE 1

The seed culture of *Streptomyces galilaeus* A-862 (FERM BP-45) was prepared by inoculating one loopful each of the agar slant culture into fifteen 500 ml flasks containing 100 ml each of seed medium (soluble starch 1.0%, glucose 1.0%, Essan Miit (soybean metal, Ajinomoto Co.) 0.1% yeast, extract 0.1%, $K_2HPO_4$ 0.1%, $MgSO_4.7H_2O$ 0.1%, NaCl 0.3%) and shake-culturing the flasks at 28° C. for 48 hours.

Fifteen liters each of fermentation medium consisting of glycerol 2.0%, soybean meal 3.0%, yeast extract 0.2%, $K_2HPO_4$ 0.1%, $MgSO_4.7H_2O$ 0.1%, NaCl 0.3%, $CuSO_4.5H_2O$ 0.0007%, $FeSO_4.7H_2O$ 0.0001%, $MnCl_2.4H_2O$ 0.0008% and $ZnSO_4.7H_2O$ 0.0002% (pH 7.4) was poured into five 30 liters jar fermentors and autoclaved under routine conditions. Three flasks each of the above-described seed culture were mixed and inoculated into the jar fermentors. Cultivation continued for 3 days at 300 rpm using an aeration rate of $\frac{1}{2}$ vol/vol/minute. The fermentation broth was collected from the five jar fermentors and centrifuged to give the mycelia and the supernatant solution. The supernatant solution was mixed well with 20 liters of chloroform and the chloroform layer was recovered. The mycelia were extracted with 30 liters of acetone and the acetone extract was concentrated under reduced pressure to about a third of the original volume. The anthracycline antibiotics were extracted from the acetone concentrate with 5 liters of chloroform. This chloroform extract was combined with the chloroform extract from the supernatant solution, and then concentrated under reduced pressure to give a crude extract containing 2-hydroxyaclacinomycins A, B, and N.

EXAMPLE 2

The crude extract from Example 1 was dissolved in ammoniacal methanol (400 ml of methanol plus 0.4 ml of conc. ammonia) and centrifuged for removal of insoluble matters. The supernatant solution was divided into four 100 ml portions. The solution (100 ml) was charged on a Sephadex LH-20 column (4.0×35 cm) and eluted with the ammoniacal methanol. The first eluting fractions of red pigment were collected from four runs of the column chromatography and concentrated to dryness under reduced pressure to give a crude preparation of 2-hydroxyaclacinomycins A, B, and N.

The crude preparation was dissolved in a small volume of chloroform; applied in a linear fashion on a pre-coated silica gel thin layer chromatographic plate for preparative use (silica gel 60 $PF_{254}$; E. Merck, Darmstadt); and developed in a solvent system of chloroform/methanol (10/1). 2-Hydroxyaclacinomycins A, B, and N gave Rf values of 0.5, 0.7 and 0.2, respectively. Each of the corresponding areas of silica gel was scraped off from the plate and eluted with a 40:10:0.1 mixture of chloroform, methanol and conc. ammonia. The eluates were concentrated to dryness in vacuo. 2-Hydroxyaclacinomycins A, B, and N were again purified by preparative silica gel thin layer chromatography using a solvent mixture of chloroform, methanol and acetic acid (150/15/1). The areas of silica gel corresponding to 2-hydroxyaclacinomycins A, B, and N were scraped off from the chromatogram and were eluted in the mixture of chloroform and methanol (5/1). The eluates were concentrated to dryness under reduced pressure and the residues were dissolved in 20 ml each of 0.2 M acetate buffer, pH 3.5. After small amounts of insoluble matters were removed by centrifugation, the supernatant solutions were washed with 10 ml each of toluene under vigorous shaking. The aqueous layers were separated; neutralized with 4N NaOH; and extracted with chloroform. After rinsing with 0.01 M EDTA solution, pH 6.0, and then with water, the chloroform extracts were dried over anhydrous sodium sulfate and concentrated to small volumes in vacuo. Excess n-hexane was added to the chloroform concentrates and the yellow precipitates were collected by filtrations. Drying in vacuo yielded 61 mg of 2hydroxyaclacinomycin A, 92 mg of 2-hydroxyaclacinomycin B and 24 mg of 2-hydroxyaclacinomycin N. The physicochemical properties of these preparations of 2-hydroxyaclacinomycins A, B, and N were as shown in the following:

2-Hydroxyaclacinomycin A

Appearance: Yellowish brown powder
Melting point: 165°–167° C.
Molecular weight: 827.9

| Elementary analysis (for $C_{42}H_{53}NO_{16}$) | | | | |
|---|---|---|---|---|
| | C | H | N | O |
| Calculated | 60.93 | 6.45 | 1.69 | 30.93 |
| Found | 60.27 | 6.20 | 1.64 | — |

Optical rotation: $[\alpha]_D^{23} +42.3°$ (c 0.04, MeOH)
Ultraviolet-visible absorption spectrum: $\lambda_{max}^{90\% MeOH}$ nm($E_1\ _{cm}^{1\%}$): 222(375), 256(235) 295(207), 450(110).
Infrared absorption spectrum (KBr): 3450, 2975, 2940, 1735, 1675, 1620, 1610, 1450, 1400, 1380, 1300, 1255, 1230, 1170, 1120, 1010.
Proton nuclear magnetic resonance spectrum (100 MHz, $CDCl_3—CD_3OD$): δ, ppm; 2.20 (6H, s, $N(CH_3)_2$); 3.65 (3H, s, $COOCH_3$); 6.20 (1H, d, J=2Hz, ArH); 6.70 (1H, d, J=2Hz, ArH); 7.30 (1H, s. ArH).

2-Hydroxyaclacinomcyin B

Appearance: Yellowish brown powder
Melting point: 186°–188° C.
Molecular weight: 825.8

Elementary analysis (for C$_{42}$H$_{51}$NO$_{16}$):

| | C | H | N | O |
|---|---|---|---|---|
| Calculated (%) | 61.08 | 6.22 | 1.70 | 31.00 |
| Found | 60.92 | 6.25 | 1.68 | 31.20 |

Optical rotation: $[\alpha]_D^{23} +97.5°$ (c 0.04, MeOH)

Ultraviolet-visible adsorption spectrum: $\lambda_{max}^{90\% \text{ MeOH}}$ nm(E$_1$ $_{cm}$$^{1\%}$): 220(580), 255(390), 293(350), 450(190), 500s(100).

Infrared absorption spectrum (KBr): 3450, 2930, 1730, 1620, 1610, 1380, 1300, 1250, 1120, 1010, 760.

Proton nuclear magnetic resonance spectrum (100 MHz, CDCl$_3$—CD$_3$OD): δ ppm: 2.20 (6H, s, N(CH$_3$)$_2$); 3.70 (3H, s, COOCH$_3$); 6.56 (1H, d, J=2Hz, ArH); 7.18 (1H, d, J=2Hz, ArH); 7.57 (1H, s, ArH).

2-Hydroxyaclacinomycin N

Appearance: Yellowish brown powder
Melting point: 167°–169° C.
Molecular weight: 829.9

Elementary analysis (for C$_{42}$H$_{55}$NO$_{16}$):

| | C | H | N |
|---|---|---|---|
| Caculated (%) | 60.79 | 6.68 | 1.69 |
| Found | 60.30 | 6.85 | 1.71 |

Optical rotation: $[\alpha]_D^{23} +103°$ (c 0.04, MeOH)

Ultraviolet-visible absorption spectrum: $\lambda_{max}^{90\% \text{ MeOH}}$ nm(E$_1$ $_{cm}$$^{1\%}$): 223(381), 256(227), 294(204), 440(113), 520s(37).

Infrared absorption spectrum (KBr): 1735, 1675, 1620, 1250, 1000.

Proton nuclear magnetic resonance spectrum (100 MHz, CDCl$_3$—CD$_3$OD): δ ppm: 2.20 (6H, s, N(CH$_3$)$_2$); 3.67 (3H, s, COOCH$_3$); 6.56 (1H, d, J=2Hz, ArH); 7.19 (1H, d, J=2Hz, ArH); 7.57 (1H, s, ArH).

What is claimed is:

1. 2-Hydroxyaclacinomycin B presented by the formula

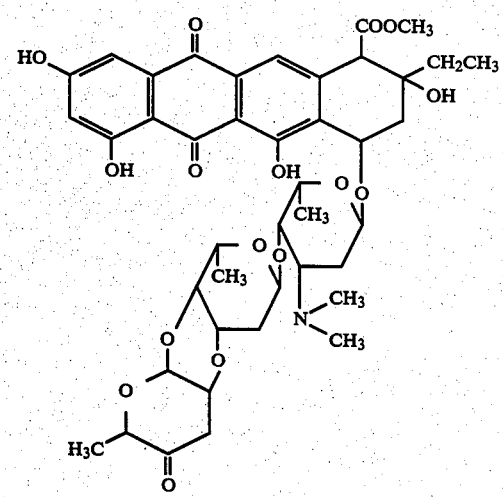

or a nontoxic acid addition salt thereof.

* * * * *